United States Patent [19]

Holtkamp

[11] Plant 4,549

[45] Jun. 17, 1980

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "OPTIMARA", Isselburg, Fed. Rep. of Germany

[21] Appl. No.: 15,824

[22] Filed: Feb. 27, 1979

[51] Int. Cl.[2] ..... A01H 5/00

[52] U.S. Cl. ..... Plt./69

[58] Field of Search ..... Plt./69

*Primary Examiner*—Robert E. Bagwill
*Assistant Examiner*—James R. Feyrer
*Attorney, Agent, or Firm*—Donald D. Jeffery

[57] ABSTRACT

An African violet known by the cultivar name Ontario and characterized by the combined features of white, violet-shaped flowers carried on strong, upright stems; very rich flower production, with 15–20 stems each carrying up to 15 flowers; early and continuous flowering, and by its large and shiny leaves.

1 Drawing Figure

The present invention comprises a new and distinct cultivar of African violet plant, botanically known as *Saintpaulia ionantha,* and hereinafter referred to by the cultivar name Ontario.

The new cultivar was referred to during the breeding and selection process by the designation C 71/1-95/79, and is the product of a planned breeding program. Ontario has very rich flowering, with the flowers being white. In a well developed plant up to 15 or more flower stems are produced each having up to 15 and more single flowers. In full bloom, the bouguet of Ontario is very full and centered above the leaves. Moreover, the plant is a continuous bloomer if properly attended to. These traits in combination were not present in previously available commercial cultivars.

The new cultivar was originated from a cross made in a controlled breeding program in Isselburg, Rhineland, Germany. The female, or seed parent was a cultivar designated Nit/Wifo medium blue. The male, or pollen parent was a cultivar designated 86/74 white star. Neither parent cultivar is patented.

The new cultivar Ontario was discovered and selected as a flowering plant within the progeny of the stated cross by me in a controlled environment in Isselburg, Rhineland, Germany.

Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Ontario, which in combination distinguish this African violet as a new and distinct cultivar:

(1) Very rich and continuous flowering, with mature plants producing up to 15 and more single flower stems.

(2) Very early flowering, with the first flowers on a very young plant appearing as soon as 4–5 weeks after potting.

(3) Upright and wiry flower stems, which when mature tend sidewards so as to permit young flower stems to grow upwardly out of the center. 15–20 stems are present in mature plants.

(4) Flowers do not drop after full maturity and dry out on flower stem.

(5) Relatively large, shiny, attractive leaves, slightly hairy and soft.

(6) White and generally violet-shaped flowers.

The accompanying photographic drawing shows a typical specimen plant of the new cultivar. The colors appearing in the photograph are as true as possible with color illustrations of this type.

In the following description, color references are made to the Royal Horticultural Society (RHS) color chart, except where general color terms of ordinary significance are obvious.

Botanical classification: *Saintpaulia ionantha,* Ramat. cv Ontario.

Parentage:

*Male parent.*—86/74 white star.

*Female parent.*—NIT/WIFO medium blue.

Propagation: The new cultivar holds its distinguishing characteristics through successive propagations by leaf cuttings and by division of shoots.

Plant: From 10 cm. to 12 cm. tall when grown in pots, and approximately 25–35 cm. in diameter when fully grown.

Leaves:

*General form.*—Oval.

*Diameter.*—65–80 mm.

*Texture.*—Soft, velvety, shiny, slightly hairy.

*Veins.*—Well pronounced on under and upperside, color 145/C.

*Color (upperside).*—Between 147A and 147B. (The true color is lighter than shown in the photograph).

*Color (underside).*—148D.

*Petiole.*—Strong, light green, hairy, color 145C.

Flowers:

*Buds.*—Bell-shaped, 6–7 mm. in diameter before opening; color is light greenish.

*Sepals.*—Color: RHS 146C. Calyx: funnel-shaped. Aspect: flower stem and receptacle connected. Peduncle: wiry, straight, hairy, color 146C.

Individual flowers:

*Size.*—30 mm. in diameter, and flat.

*Color.*—Upperside: clear white. Underside: clear white (also slightly hairy).

*Borne.*—Fifteen (15) or more flower stems each carry up to 15 and more single flowers.

*Shape.*—Typical violet-shaped; 2 small, 3 large petals, with the petal surface having a glittering appearance and the edges of the petals being slightly hairy; a few flowers have an additional small petal connected to the filament.

*Arrangement.*—On strong wire-like stems, slightly hairy.

*Flowering time.*—In 4–5 weeks after potting a well developed starter plant the first flowers appear, and thereafter the plant blooms continuously.

Reproductive organs:

*Stamens.*—Two in number.

*Anthers.*—Four anther cells, color 8C.

*Arrangement.*—Joined together.

*Filaments.*—2–3 mm. long, white in color.

*Styles.*—6–8 mm. long, white in color; seed capsule pushed slightly through, color light green.

*Pollen color.*—8D.

Roots: Well developed, strong.

Disease resistance: No disease problems noted to date.

General observations: Ontario is a unique new variety of African violet. It blooms very quickly, in rich abundance, and flowering is continuous. The pure white flowers are on upright stems thereby producing a massive flower bouquet well above the leaves. As more stems are produced, the older stems are forced outwardly thereby expanding the diameter of the bouquet, with the plant reaching 35 cm. in diameter when fully grown.

I claim:

1. A new and distinct cultivar of African violet, as shown and described, known by the cultivar name Ontario and characterized by the combined features of white, violet-shaped flowers carried on strong, upright stems; very rich flower production, with 15–20 stems each carrying up to 15 flowers; early and continuous flowering, and by its large and shiny leaves.

* * * * *

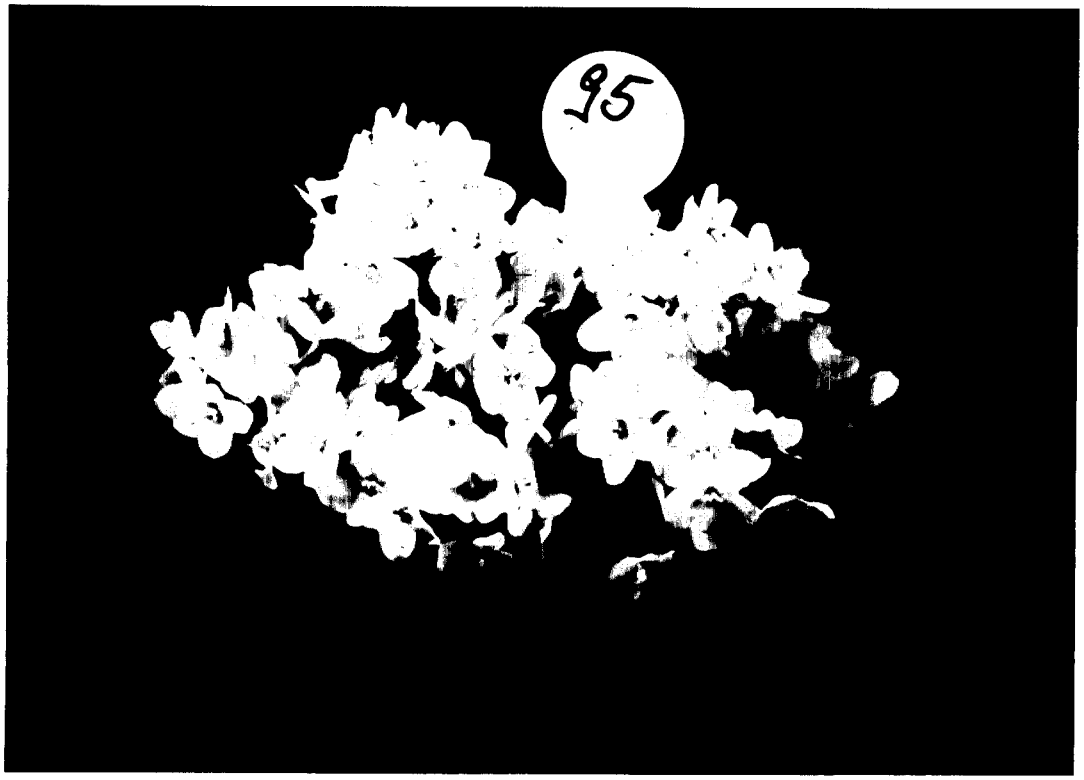
95